United States Patent [19]

Robert et al.

[11] Patent Number: 5,919,919
[45] Date of Patent: Jul. 6, 1999

[54] BRASSICA SP. GENE PROMOTER HIGHLY EXPRESSED DURING TAPETUM DEVELOPMENT

[75] Inventors: Laurian Robert, Gatineau; Hai Ping Hong, Saskatoon, both of Canada

[73] Assignees: Her Majesty the Queen in right of Canada, as represented by Agriculture and Agri-Food Canada, Ottawa; National Research Council of Canada, Saskatoon, both of Canada

[21] Appl. No.: 08/595,937

[22] Filed: Feb. 6, 1996

[51] Int. Cl.[6] .......................... C07H 21/00; C12P 21/00; A01H 3/00; C12N 5/14
[52] U.S. Cl. .................. 536/24.1; 536/23.6; 435/69.1; 435/410; 435/419; 435/320.1; 800/200; 800/205
[58] Field of Search ................. 536/24.1, 23.6; 435/69.1, 410, 419, 320.1; 800/205, 200

[56] References Cited

U.S. PATENT DOCUMENTS

| | | | |
|---|---|---|---|
| 5,401,836 | 3/1995 | Baszczynski et al. | 536/24.1 |
| 5,612,472 | 3/1997 | Wilson et al. | 536/24.1 |
| 5,659,026 | 8/1997 | Baszczynski et al. | 536/24.1 |
| 5,689,053 | 11/1997 | Robert et al. | 800/205 |

FOREIGN PATENT DOCUMENTS

| | | | |
|---|---|---|---|
| 2099125 | 6/1992 | Canada | C12N 15/11 |
| 2099482 | 1/1994 | Canada | C12N 15/82 |
| WO 92/18625 | 4/1992 | WIPO | C12N 15/11 |
| WO 92/13957 | 8/1992 | WIPO | C12N 15/82 |
| WO 93/25695 | 6/1993 | WIPO | C12N 15/82 |
| WO 94/25593 | 11/1994 | WIPO | C12N 15/29 |

OTHER PUBLICATIONS

Abstract, "Transformation of *Brassica Napus* with the GUS Reporter Gene Under the Regulation of Tissue–Specific Promoters", Hong, H.P., et al., Abstracts VIIIth International Congress of Plant Tissue and Cell Culture, Firenze, Jun. 12–17, 1994.

*Primary Examiner*—Ponnathapura Achutamurthy
*Assistant Examiner*—Phuong T. Bui
*Attorney, Agent, or Firm*—Rothwell, Figg, Ernst & Kurz, P.C.

[57] ABSTRACT

A Brassica sp. genomic clone containing a gene promoter, which directs expression in the tapetum, was isolated. When the promoter was fused with the GUS gene and introduced into *B. napus* by Agrobacterium mediated transformation, this promoter controlled GUS expression in the tapetum in transgenic *B. napus* plants. Expression was observed from bud length 2–3 mm, which corresponds to the uninucleate microspore stage, peaked at 4–5 mm which corresponds to the binucleate microspore stage and declined to no detectable level at the open flower stage. There was no GUS expression in other tissues such as root, stem, leaf, sepal, petal or pistil. This promoter will be useful for the temporal and spatial control of gene expression in plants.

15 Claims, 4 Drawing Sheets

Figure 1

```
         10         20         30         40         50         60
          |          |          |          |          |          |
   1 GAGCTCCACC CACAGAAGCA GATAAACCAG CTGAAGGAAC AACAGAAAAA CCAAAAGATA

61 ATTCGACTGG AGGAGCAGCC GATAAACCAG AAGATAAACC AGTTGGAGGA GCAGCCGATA

121 AACCAGAAGG TAAACCGGAT GGAGGAGCAA CAAATAAGCC AGAAAGTAAA CCAGCTGGAG

181 GACCATCAAA TAAACCAAAA GATAAACCCG CTGGAGGACC AACGGATAAA CCAGAAAGTA

241 AGCCAGCAGA TAAACCCGCT GGAGGACCAA CAGATAAGCC AGGAAGTAAA CCGGTTGATA

301 AACCCGCTGG AGGACCAACA GATAAGACAG AAAGTAAACT GGTTGGAGAG GCATCAAATA

361 AACCAAAAGA TAAACCCGCT GGTGGATCAA CAGATATGCC AGAAGCTGGA GAGACATCAA

421 ATAAACCAAA AGATAAATCC GTTGGAGGAC CAACAAATAA GCCAGAAAGT AAACCAGCTG

481 GAGAAACATC ACATAAACCA AAAGATAAAC CCGCTGGTGG ACCAACAGAT AAGCCAGAAA

541 GTAAACCGGC TGGAGAAACA TCACATAAAC CAAAGATAA ACTCGCTGGT GGACCAACAG

601 ATAAGCCAGA AAGTAAACCA GCTGGAGAGG CATCAAATAA ACCAAAAGAT AAACCCGCTG

661 GTGGACCAAC AGATAAACCA GCTGGAGGAT CAGTAGATAA ACCAAAAGAT AAACCTGCCG

721 GAGGACCAAC AGATAAACCA ACAAATAAAC CGACTGGAGG GGCTGCAAAT AAACCGGCTG

781 GAGAGGCAGC AAACAAACCG ACTGGAAAAC CGAAAAATAA ACCGGCTGGA GAGAATAAAC

841 CACCGGGATG GTATAGGTGA ATGGAGTAGT ATGAAATTAA AGTATTGGGT TCCACAAATT

901 ATTCCTAATT TATCCTACAC TACATGTTTC ATAATCATTT CTATAAATGT ACGACTTGTT

961 ACAAAGAAAT GATAAACAGT GTACAGAATT TTCTTTGTAA ATTTATTAAA TTGATGTGGA

1021 TATCATTATA ACTGACGTTA GCGTATATCG ACCAATGCGA TAACCAAATC ATCGGTATAT

1081 ACCTAAGACT TCCTTTTTAA AAATGAATCT GATACTAATT TAATGTACGA CTTCCAATAA

1141 CCAATCTTCT TGCATTTTTC ATTGCCATTT ACCTTGAACG CCTCTCTTTC TAGTATGAGA

1201 CATTAACATT GCGCTCTTGT CACAATGAAG CCATGGAAAA CTTCGGCTCT TTAATCACAC

1261 ATGTGACAAT CCAGTTGGTT TAAGGGAAAG TATTTTATAT TTTATATAGC TCGTTCTCAG

1321 AACAAAAAAA CCAAATTCTT TAGCAAAAAT GGTCCTTAAG GCCCATTCCG TTTCTTCTTA

1381 TAATGTTCTG GGCTAGCCCA TTTGAATTTA AACCTTTCCT TTCAATTTCT GCATTAATAT

1441 AATTCAGTTG TTCAAAAAAA AAATAGCGCT TATTGAAATA ATAGAGAGAA AGATAATGAG

1501 AAGGGAGAAA ATGAAAAGCG TATTTCATAT GAGAGATTGT CAACAAAAAT TGAGTGACTT

1561 TTATGATATT TGTTCAAAGA ATAGTCTAAT AACCTTTCTT ATTTAAATTT TAATTATGTT

1621 ATATATCAAT AATACTAAAA TAATTAGTTA CTCACAGTTC GTGACAAAAA AAAAAGCAAA

1681 TAGATGAAAT GAAATGAAAG AAAGATCTTT CTTCACGCGT TGATATTCAT AAAACAATGG

1741 AATGAAAGAA AACAGTTAAG ATTCTACAAG AAAGAAAAGA AAGTCCCAAA AACATGACAA

1801 ATAGATGAAG AAGCAAATGT GACTTGACGT AACGTAGAAC TCCATATATA CTCCCATCGT

1861 TTTGCATGGA GCATGCATGT GTACCGTGCA CGTCGTAGAC CACACAACTC CTTCATAAAA
                                           ←─┐
1921 AGCCCTCTCT CTTCCCATCA CCAAACCATC AGAAAATATG
```

Sta41-6 (SINGLE COPY):

Sta41-32 (SINGLE COPY):

Sta41-11 (DOUBLE COPIES):

Sta41-35 (DOUBLE COPIES):

BRASSICA SP. GENE PROMOTER HIGHLY EXPRESSED DURING TAPETUM DEVELOPMENT

The present invention relates to plant gene promoters. Specifically this invention relates to a gene promoter that directs high levels of transcription in the tapetum.

BACKGROUND OF THE INVENTION

Pollen production in flowering plants is a highly regulated developmental process which occurs within the diploid sporophytic tissue of the anther. The normal development of the male gametophyte is dependent upon the tapetum which lines the locular space of the anther. The tapetum is thought to provide the developing microspore/pollen with nutrients and other necessary products such as enzymes and structural components (Pacini et al., *Plant Syst. Evol.*, 149:155–185, 1985). The importance of the role of the tapetum is illustrated by the fact that male sterility can result from tapetal malfunction (Kaul, *Male Sterility in Higher Plants*, 1988; Koltunow et al., *Plant Cell*, 2:1202–1224, 1990; Mariani et al., *Nature*, 347:737–741, 1990).

In Brassica, the secretory tapetum is composed of cells which are metabolically very active until approximately microspore mitosis at which time they degenerate (Grant et al., *Can. J. Bot.*, 64:779–786, 1986; Murgia et al., *Sex Plant Reprod.*, 4:28–35, 1991; Polowick and Sawhney, *Sex Plant Reprod.*, 3:263–276, 1990). Their cellular contents such as lipids are then released into the anther locule where they are thought to contribute to the formation of the external pollen coat (Evans et al., *Planta*, 186:343–354, 1992; Heslop-Harrison, *New Phytol*, 67:779–786, 1968). In the Brassica napus cv. Westar used in the present invention, the tapetal lipids accumulate in small lipid bodies of less than 1 $\mu$m in diameter which are either free or in membrane-bound clusters (Polowick and Sawhney, *Sex Plant Reprod.*, 3:263–276, 1990). Membrane-bound oil bodies of similar size have been well characterized in seed storage tissues where they were found to be associated with specialized proteins called oleosins (Huang, *Ann. Rev. Plant Physiol. Plant Mol. Biol.*, 43:177–200, 1992; Murphy, *Prog. Lipid Res.*, 32:247–280, 1993). Oleosins are believed to help stabilize the small oil bodies during dehydration and possibly provide binding sites for lipase activity upon germination. Recently, a novel class of oleosins was shown to be associated with the lipid bodes of B. pollen grains where they are believed to serve a similar function (Roberts et al., *Plant J.*, 3:629–636, 1993). Putative oleosins have also been reported in the anthers of *Arabidopsis thaliana* (De Oliveira et al., *Plant J.*, 3:495–507, 1993).

Two highly homologous Brassica napus flower cDNA clones, Sta 41-2 and Sta 41-9, were isolated and characterized (Robert et al, *Plant J.*, 1994, 6:927–933). These clones were shown to correspond to genes expressed in the tapetum from the early uninucleate microspore stage to the dinucleate stage. The predicted Sta 41-2 and Sta 41-9 proteins possessed characteristics similar to oleosins such as a polar N-terminal domain, a large relatively conserved hydrophobic domain and a long C-terminal domain which consisted of four different groups of repeats. In addition, like oleosins, the Sta 41-2 and Sta 41-9 proteins have a basic pI, lack of a signal peptide and are found in a tissue which accumulates lipids in small lipid bodies.

Tapetal-specific cDNAs have been isolated from *Anthirrhinum majus* (Nacken et al., *Mol. Gen. Genet.* 229:129–136, 1991; Nacken et al., *FEBS Lett.* 280:155–158, 1991), *Brassica napus* (Scott et al., *Plant Mol. Biol.* 17:195–207, 1991; Shen and Hsu, *Mol. Gen. Genet.* 234:379–389, 1992; Hird et al., *Plant J.* 4:1023–1033, 1993; Robert et al., *Plant J.* 6:927–933, 1994), *Sinapis alba* (Staiger and Apel, *Plant J.* 4:697–703, 1993), maize (Wright et al., *Plant J.* 3:41–49, 1993), tobacco (Koltunowetal., *Plant Cell* 2:1201–1224, 1990), tomato (Smith et al., *Mol. Gen. Genet.* 222:9–16, 1990) and rice (Tsuchiya et al., *Plant Mol. Biol.* 26:1737–1746, 1994). The identity and/or function of the products encoded by most of these tapetum-specific transcripts are unknown.

Only three tapetum-specific genes and their regulatory sequences have been studied in detail: TA29 from tobacco (Koltunow et al., *Plant Cell*, 2:1201–1204, 1990; Mariani et al., *Nature*, 347:737–741, 1990), tapl from *Antirrhinum majus* (Spena et al., *Theor, Appl. Genet.* 84:520–527, 1992; Nacken et al., *Mol. Gen. Genet.* 229: 129–136, 1991) and A9 from *Arabidopsis thaliana* (Paul et al., *Plant Mol. Biol.* 19:611–622, 1992). However, the cis elements required for tapetal gene expression are still not known. The temporal expression pattern of the Sta 41 promoter was somewhat different from the above mentioned tapetalspecific promoters, which were all expressed during the early stages of pollen development from meiosis to late microspore interphase or early mitosis, corresponding well with the timing of tapetum cell differentiation and degeneration. The temporal expression pattern of the Sta 41 promoter was evident from the uninucleate microspore stage to the early trinucleate stage in pollen development, by which time the tapetum had exhibited considerable signs of degeneration (Grant et al., *Can. J. Bot.*, 64:779–786, 1986; Murgia et al., *Sex Plant Reprod.*, 4:28–35, 1991; Polowick and Sawhney, *Sex Plant Reprod.*, 3:263–276, 1990).

SUMMARY OF THE INVENTION

The present invention relates to plant gene promoters. Specifically this invention relates to a promoter that directs high levels of transcription in the tapetum.

In one embodiment of the present invention there is provided a Brassica sp. gene promoter that directs high levels of transcription in the tapetum.

The present invention is also directed to a chimeric gene construct comprising the Brassica gene promoter of the present invention and the coding sequence of a gene, for which tapetum-directed expression is desired.

The present invention is further directed to a method of conferring tapetum-directed expression of a gene in a plant, comprising:

operatively linking a gene, for which tapetum-directed expression is desired, with a Brassica sp. gene promoter of the present invention to produce a chimeric gene;

introducing the chimeric gene into an appropriate vector; and introducing the vector into a plant capable of expressing the chimeric gene.

The present invention is further directed to transgenic plants containing a chimeric gene construct as described above.

BRIEF DESCRIPTION OF THE DRAWINGS

These and other features of the invention will become more apparent from the following description in which reference is made to the appended drawings wherein:

FIG. 1 is the nucleotide sequence of the 5' upstream region containing the promoter fragment of the *B. napus* tapetum-expressed gene, which corresponds to SEQ ID NO: 1. The ATG start codon is underlined. This promoter fragment up to position 1952 was used with the GUS fusion construct.

Figure 2A:
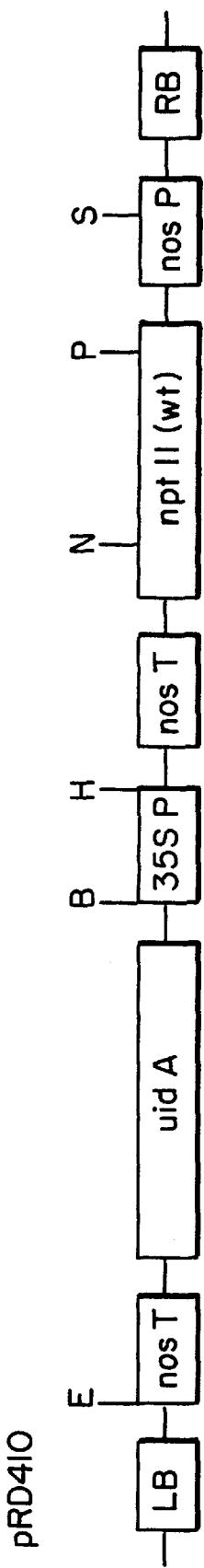
Figure 2B:
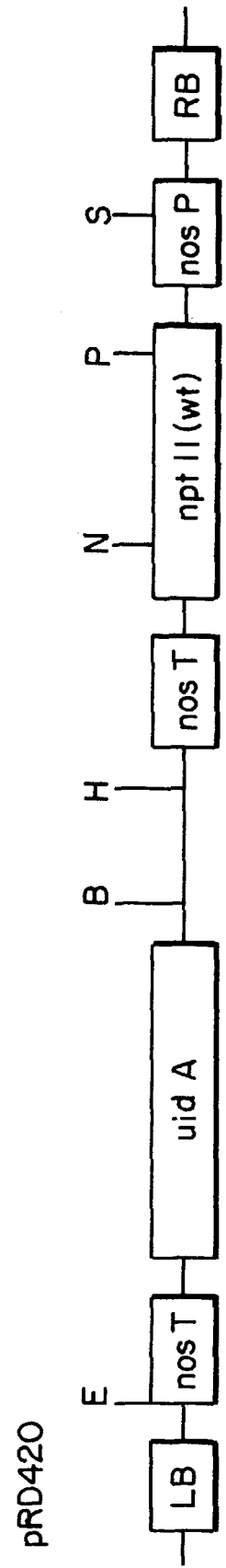
Figure 2C:
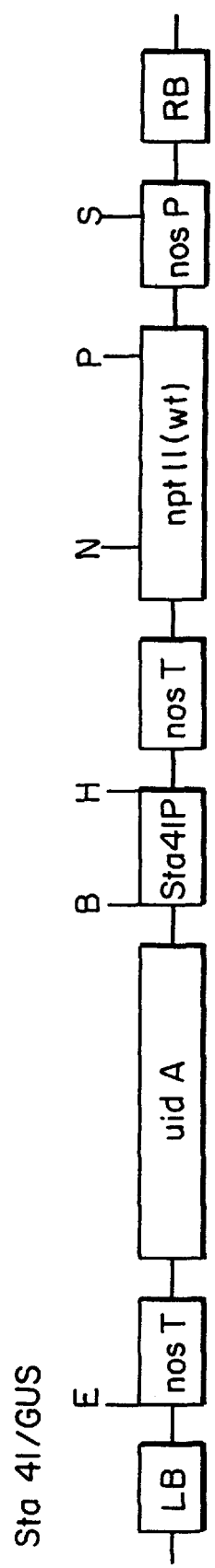

FIG. 2 shows the construct of plasmids pRD410 (FIG. 2B), pRD420 (FIG. 2A) and Sta 41/GUS (pRD 420 containing the Sta 41 promoter FIG. 2A).

Figure 3A:
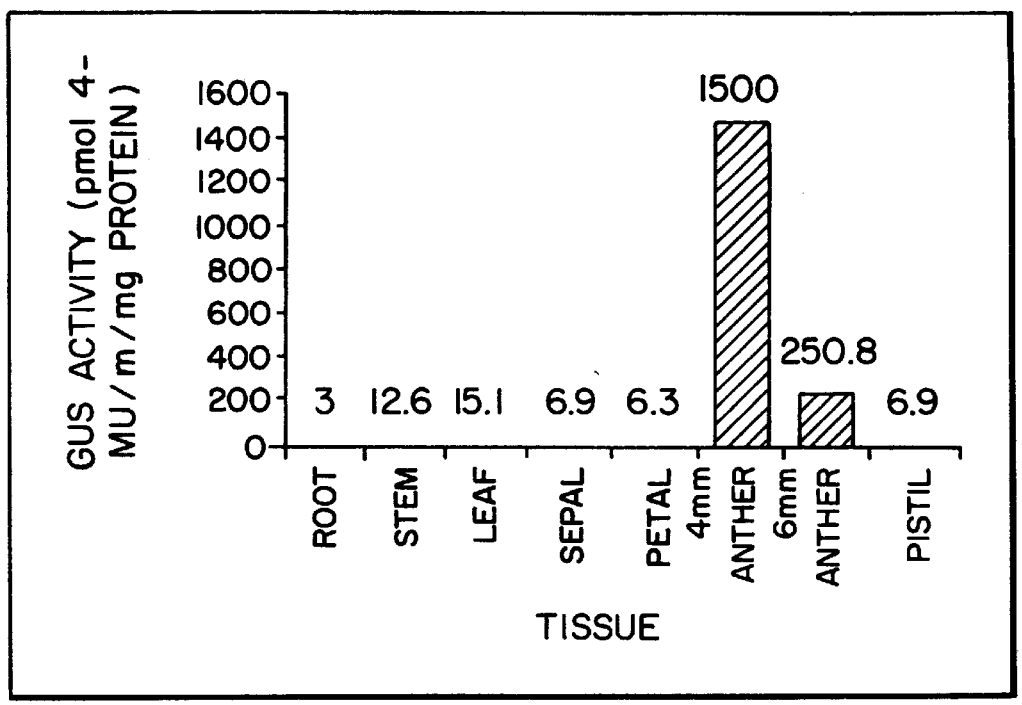
Figure 3B:
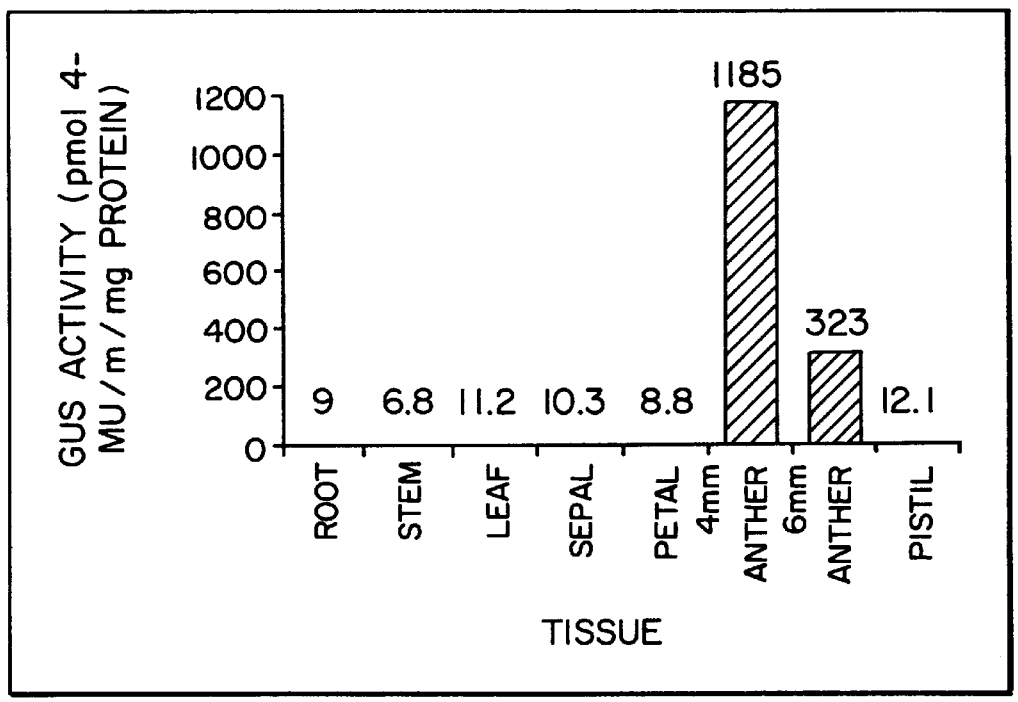
Figure 3C:
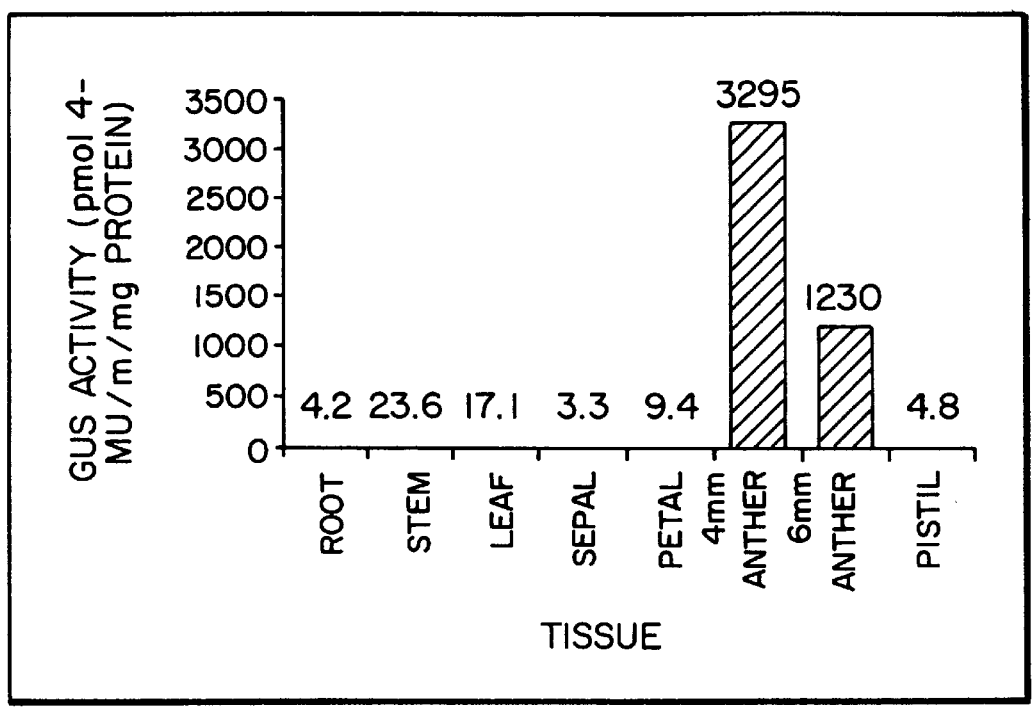
Figure 3D:
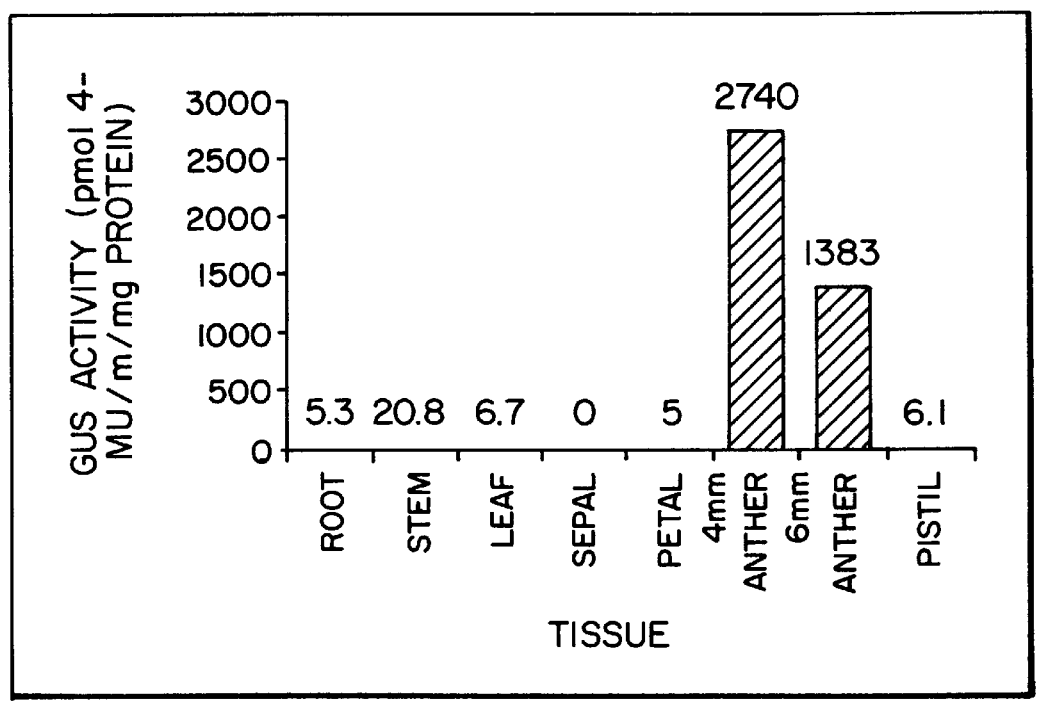

FIG. 3 shows the fluorometric GUS activity in a Sta 41/GUS transgenic plant, wherein FIG. 3A is transgenic plant number 6 with a single insertion; FIG. 3B is transgenic plant number 32 with a single insertion; FIG. 3C is transgenic plant number 11 with a double insertion and FIG. 3D is transgenic plant number 35 with a double insertion.

DESCRIPTION OF PREFERRED EMBODIMENT

The present invention relates to plant gene promoters. Specifically this invention relates to a gene promoter that directs high levels of transcription in the tapetum.

In the context of this disclosure, the term "promoter" or "promoter region" refers to a sequence of DNA, usually upstream (5') to the coding sequence of a structural gene, which controls the expression of the coding region by providing the recognition for RNA polymerase and/or other factors required for transcription to start at the correct site.

The present invention is directed to a promoter which facilitates the spacial and temporal expression of a gene in the tapetum. Specifically, the present invention is directed to a gene promoter isolated from Brassica sp. The promoter, in its native form, has been predicted to control the expression of an oleosin-like gene in Brassica sp. tapetum.

One embodiment of the present invention is directed to a promoter isolated from *Brassica napus*. Substantial homology has been demonstrated between *Brassica napus* and other species of Brassica. Thus, the present invention is not limited to the promoter isolated from *Brassica napus*, but includes within its scope the corresponding promoter from other species of Brassica.

The present invention is further directed to a chimeric gene construct containing a gene of interest wherein said gene is operatively linked to the promoter of the present invention. Any gene can be used and manipulated according to the present invention to result in the tapetum-directed expression of said gene.

Many genes important to tapetum development could be used according to the present invention to cause male sterility, for example, for the purpose of hybrid seed production. The Sta 41 tapetum-expressed gene itself could be used. If this gene is critical to tapetal or pollen development, expressing an antisense version or a sense version (in this case the inhibition would occur by co-suppression) of this gene in the tapetum could reduce the Sta 41 gene activity and result in male sterility. Genes coding for products which would disrupt the development of pollen or tapetal cells could also be used to cause male sterility according to the present invention. For example, the promoter of the present invention could be fused to a gene encoding the diphteria toxin A chain (Thorsness et al., *Dev. Biol.*, 143:173–184, 1991) or a RNAse (for example, Barnase from *Bacillus amyloliquefaciens*, Hartley, *Gene*, 53:11–20). The promoter could also be useful for example, to target the expression of genes which would alter the composition of pollen to make it less attractive to pest or to make it more nutritional.

In the context of the present disclosure, the term "operatively linked" is meant to mean that the various components of the chimeric gene construct of the present invention are positioned so as to ensure the proper transcription, or transcription and translation of the desired sequence. For example, a chimeric gene could be constructed by replacing the coding region of the genomic clone Sta 41 G10 with the complete or partial coding region of another gene in the sense or anti-sense orientation. A chimeric gene could also be constructed by replacing a specific promoter with the promoter of the present invention in such a way as to allow the proper transcription, or transcription and translation of a particular sequence in anthers.

The chimeric gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene. The 3' untranslated region from the structural gene of the present construct can also be used.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be of a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase, uid A), or luminescence, such as luciferase are useful.

Also considered part of this invention are transgenic plants containing the chimeric gene construct of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Any plant species can be modified according to the present invention to include the chimeric gene construct to provide anther-, specifically tapetum-directed expression of a gene.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421–463 (1988); and Grierson and Corey, *Plant Molecular Biology*, 2nd Ed. (1988). The present invention further includes a suitable vector comprising the chimeric gene construct.

When specific sequences are referred to in the present invention, it is understood that these sequences include within their scope sequences that are "substantially homologous" to said specific sequences. Sequences are "substantially homologous" when at least about 80%, preferably at least about 90% and most preferably at least about 95% of the nucleotides match over a defined length of the molecule. Sequences that are "substantially homologous" include any substitution, deletion, or addition within the sequence. DNA sequences that are substantially homologous can be identified in Southern hybridization experiments, for example under stringent hybridization conditions (see Maniatis et al., in Molecular Cloning (A Laboratory Manual), Cold Spring Harbor Laboratory (1982) p 387 to 389). Such substantially homologous sequences have been found in Brassica sp.

The specific sequences, referred to in the present invention, also include sequences which are "functionally equivalent" to said specific sequences. In the present invention functionally equivalent sequences refer to sequences which although not identical to the specific sequences provide the same or substantially the same function. Sequences that are functionally equivalent include any substitution, deletion or addition within the sequence. With reference to the present invention functionally equivalent sequences will also direct the expression of a gene to the tapetum.

While this invention is described in detail with particular reference to preferred embodiments thereof, said embodiments are offered to illustrate but not limit the invention.

EXAMPLES

Example 1
Isolation of the *B. napus* Genomic Clone Containing a Tapetum-Expressed Gene The spring *B. napus* cv. Westar genomic library was constructed in the vector λ DashII as recommended by the manufacturer (Stratagene). Genomic DNA was extracted from nuclei (Jofuku and Goldberg, 1988, in *Plant Molecular Biology*:a practical approach, 37–66), partially digested with Sau 3A and size fractionated (9–20 kb) as described in Unit 5.3-*Current Protocols in Molecular Biology* (1987). The genomic library (300,000 plaque forming units) was probed with the [$^{32}$P]oligolabelled Sta 41 cDNA clone (Robert et al., *Plant J.*, 6:927–933, 1994). A genomic clone, Sta 41 G10, containing a sequence identical to the *B. napus* tapetum-expressed oleosin gene Sta 41-9 was isolated and characterized.

A Sac I/Hind III fragment containing the 5' upstream region of the Sta 41 gene was subcloned into pGEM 4Z (Promega) and used to generate the Sta 41 promoter fragment. The sequence of this promoter fragment is shown in FIG. 1 (SEQ ID NO: 1). The sequence of this promoter fragment as found in its native form, is as depicted in FIG. 1. For a reference, the initiation codon ATG from the Sta 41 is also shown and underlined in FIG. 1. For the promoter-GUS fusion constructs, the promoter fragment used is that as shown in FIG. 1, up to the nucleotide position 1952, as shown by the arrow in FIG. 1. This promoter fragment (1952 bp) was obtained by the polymerase chain reaction (PCR) using the primer 5'-Sta 41 III, 5'ATAGGATCCTGATGGTTTGGTGATGGG-3' (SEQ ID NO: 2) which is complementary to sequence -6 to -24 bp upstream of the translational start ATG in Sta 41 GIO (and to which a Ban HI site was added) and the SP6 promoter primer found in the pGEM 4Z plasmid.

Amplifications were performed in a 100 μl volume containing 1X Taq DNA polymerase buffer (Promega)/1.5 mM MgCl$_2$/0.2 mM dNTPs/250 ng of each primer/1 ng of the subcloned DNA. Following 5 min. at 95° C., 2.5 U of Taq polymerase was added and 35 cycles of 1 min. at 95° C., 1 min. at 42° C., 2 min. at 72° C. were performed and followed by a 10 min. extension at 72° C. The Sta 41 promoter/PCR fragment was identified by sequencing and then subcloned as a Barn I/Hind III fragment upstream of the GUS gene of the binary vector pRD 420 (FIG. 2) for use in plant transformation.

Example 2
Agrobacterium-mediated Plant Transformation with Sta 41/GUS

Plasmid pRD 410 was used as a positive control and has a GUS (β-glucuronidase) gene under the control of a CaMV 35S promoter and for transformed plant selection the NPT II (neomycin phosphotransferase II) gene under the control of the nos (nopaline synthase) promoter (R. S. S. Datla et al., *Gene*, 211:383–384 (1992)). Plasmid pRD 420 was used as a negative control and is similar to pRD 410, but lacks the CaMV 35S promoter. Plasmid Sta 41/GUS contains the 1952 bp fragment from the tapetum expressed oleosin-like gene (Sta 41 G10). These plasmids are depicted in FIG. 2.

The recombinant plasmid DNAs were introduced directly into the *Agrobacterinum tumefaciens* strain GV3101:pMP90 following the protocol supplied with Pharmacia Agrobacterium cells (product: # 27–1535). To prepare the Agrobacteriwn competent cells, 5 ml of YEP media (10 g yeast extract, 10 g peptone, 5 g sodium chloride (NaCl) per liter, pH 7.0) with 150 μg/ml rifampicin (chromosomal marker) and 100 μg/ml gentamycin (pTi marker) was inoculated with a loopful of a glycerol stock of *Agrobacterium tumefaciens* GV 3101:pMP90 and cultured at 28° C. by shaking at 250 rpm approximately 15 h. The next day, 2 ml of the overnight culture was added to 50 ml of fresh YEP media and grown at 28° C. to reach an O.D. of 0.5–1.0 (at 600 nm). The culture was then chilled on ice for 10 min. and centrifuged at 5,000 rpm in a Sorvall SS34 for 5 min. The cells were resuspended in 1 ml cold 20 mM CaCl$_2$. These competent cells were dispensed into prechilled 1.5 ml Eppendorf tubes in 100 μl aliquots and frozen at -80° C. until further use.

The Agrobacterium cells were transformed as follows. One μg of uncut plasmid DNA (pRD 410, pRD 420 or Sta 41/GUS) in water was added to 100 μl of Agrobacterium competent cells and incubated on ice for 30 min. The cells were then frozen in liquid nitrogen and thawed quickly at 37° C. for 5 min. and 1 ml of YEP medium was added to the cell/DNA mixture and incubated at 28° C. for 2 h with gentle shaking (100 rpm). Cells were then centrifuged in a microfuge for 30 s, the supernatant was poured out and the pellet resuspended in the remaining supernatant (50–100 μl). The resuspended cells were spread onto a YEP plate with 150 μg/ml rifampicin, 100 μg/ml gentamycin and 50 μg/ml kanamycin and incubated at 28° C. for 2–3 days.

Plasmid DNA from individual Agrobacterium colonies was digested with Eco RI and Hind III or Hind III and Bam HI, respectively, along with RNase A at 37° C. for 2 h and analyzed by gel electrophoresis in 0.8% agarose. Colonies which contained recombinant plasmid were selected and grown overnight in 5 ml AB minimal medium with 50 µg/ml kanamycin and 50 µg/ml gentamycin. The overnight culture was centrifuged at 4500 rpm for 15 min. and the cells were resuspended in 1 ml of double distilled water or 10 mM $MgSO_4$ (with 7% DMSO stocks could be kept at −70° C. for further use).

Agrobactetium-mediated transformation of B. napus cv. Westar was performed according to the method of Moloney et al., Plant Cell R., 8:238–242, (1989), with minor modifications. Seeds were sterilized by brief wetting in 95% ethanol then 70% commercial bleach (Javex) with a drop of detergent (Tween 20) for 15 min. with occasional agitation; 0.025% mercuric chloride with a drop of Tween 20 for 10 min. and finally rinsed well with sterile distilled water at least 3 times. Thirty to forty seeds were plated on ½ strength hormone-free MS medium (SIGMA) with 1% sucrose in 15×60 mm petri dishes. They were then placed, with the lid removed, into a sterilized Majenta GA7 jar and were kept at 25° C., with 16 h light/8 h dark and a light intensity of 70–80 µE.

Cotyledons were excised from 4-day old seedlings by gently grasping both petioles just above the point where they join the hypocotyl. The cut edge was dipped briefly into an overnight Agrobacterium culture containing the recombinant plasmid DNA and 50–60 cotyledons were placed in each plate containing Medium I [4.57 g/l M.M.O. (GIBCO BRL), 3% sucrose, 4.5 mg/l benzyl adenine (BA), 0.7% phytagar (GIBCO BRL), pH 5.8]. After three days of cocultivation explants were transferred to plates containing Medium II [4.57 g/l M.M.O., 4.5 mg/l BA, 3% sucrose, 0.7% phytagar, pH 5.8. Carbenicillin (500 mg/l) was added after autoclaving]. After 7 days the explants were transferred to plates containing Medium HI [4.57 g/l M.M.O., 4.5 mg/l BA, 3% sucrose, 0.7% phytagar, pH 5.8, carbenicillin (500 mg/l) and kanamycin (20 mg/l)]. The plates were cultured for 2–3 weeks at which time green shoot buds could be identified; these were directly transferred to glass jars containing Medium IV [4.44 g/l MS/B5 (SIGMA), 0.1 mg/l NAA, 3% sucrose, 0.7 phytagar, pH 5.8, (500 mg/l) carbenicillin and (50 mg/l) kanamycin added after autoclaving]. Once a good root system had developed, the plantlets were removed from jars, most of the agar was removed from the roots and then transferred to moist potting soil.

Transformants were screened to confirm the presence of the T-DNA by using a [$^{32}$P]oligolabelled fragment of the GUS gene using standard Southern hybridization procedures (Sambrook et al., in Molecular Cloning (A Laboratory Manual), 2nd Ed. Cold Spring Harbor Laboratory (1989)).

As shown by histochemical staining, the 1952 bp Sta 41 promoter was sufficient to direct the tissue-specific expression of the GUS gene in the anthers. The promoter Sta 41 expressed exclusively in the anther, and more specifically in the tapetum. No GUS activity was detected in roots, stem, leaf, sepal, petal, pollen or pistil at flowering (results not shown).

The negative control plants which were transformed with the promoterless/GUS vector pRD 420 did not give any GUS expression within 1–2 days of incubation, however, after 2–3 days of X-Gluc staining, a couple of plants showed weak GUS expression in some root regions. The positive control plants which contain the CaMV 35S/GUS vector pRD 410 showed varying levels of GUS expression among six transgenic plants. It was generally found that GUS expression occurred in most tissues under the control of the 35S promoter, although there were some minor differences in the degree of GUS expression at different stages (results not shown).

In B. napus plants grown under equivalent conditions, the length of the flower bud is a good indicator for the developmental stage of the microsporocytes. Most microspores are at the same stage of development in anthers of flower buds of the same length (Albani et al., Plant Mol. Biol., 15:605–622 (1990)). Transgenic plants containing the tapetum-expressed Sta 41 promoter were selected and assayed histochemically for GUS activity in the floral organs following the methods of Jefferson et al., Plant Mol. Biol. Rep., 5:387–405 (1987). The flower organs (sepal, petal, stamen and pistil) of a series of different bud sizes (2–6 mm buds and open flower) from each of the six plants as well as whole root segments and hand sections of stem and leaf were dissected and placed in a 24-well tissue culture plate containing 300–500 µl of reaction buffer. The reaction buffer contained 1 mM X-Gluc (5-bromo-4-chloro-3-indolyl-β-D-glucuronic acid, Sigma) in 0.1M sodium phosphate, pH 7.0, 10 mM EDTA, 0.1% Triton X-100 and 0.5 mM potassium ferricyanide, 0.5 mM potassium ferrocyanide. The staining reaction was carried out at room temperature for 1 h to overnight depending on the intensity of staining. GUS activity was scored as +, ++ or +++ depending on the intensity of GUS staining. In all cases, GUS expression was only observed in anthers and not in other organs. Using this method, GUS expression was first detected at a bud length of 2–3 mm which corresponds to the uninucleate microspore stage, peaked at 4–5 mm which corresponds to the binucleate microspore stage and then no detectable activity in open flowers corresponding to the stage of the pollen (Table 1).

TABLE 1

Temporal expression of Sta 41/GUS in anthers of transgenic B. napus

| Transgenic line no. | 2 mm | 3 mm | 4 mm | 5 mm | 6 mm | open flower |
|---|---|---|---|---|---|---|
| 1 | − | + | +++ | ++ | + | − |
| 5 | −, + | + | ++ | +++ | + | − |
| 6 | − | − | ++ | + | ++ | − |
| 11 | − | +++ | ++ | − | − | − |
| 23 | − | +++ | +++ | ++ | ++ | − |
| 35 | − | +++ | +++ | ++ | − | − |

+++ strong activity; ++ high activity; + low activity; +,− inconsistent activity; − no activity To verify the cellular localization of the Sta 41 promoter activity, cryosections of buds from approximately 1 mm in length to approximately 5 mm in length, and also from open flowers were examined in a histochemical assay. Anthers from transgenic plants at different developmental stages were mounted in cryomold (25×20×5 mm) using frozen tissue embedding media (Tissue-Tek II OCT compound) and sectioned at −20° C. using a 2800 Frigo cut cryostat II (Reichert-Jung, FRG). Sections were picked up and melted on a slide, and then stained with X-Gluc (same as above) at 37° C. for half an hour to one hour, then sections were carefully washed with ethanol and directly mounted for microscopy (Leitz Microscope). GUS activity was determined in anthers at various stages of male gametophytic development. These studies further confirmed the developmental pattern of expression. Using this method, there was no detectable GUS expression during the sporogenesis phase (1–2 mm); and very low expression was observed at the microspore interphase (2–3 mm). GUS expression steadily increased at the uninucleate stage (3–4 mm), reached a plateau at the binucleate stage and high levels of GUS activity were observed in the degenerating tapetum (5 mm). No GUS expression was observed in anthers at the late trinucleate microspore stage or in the mature pollen grains (results not shown).

A fluorimetric quantitative assay for GUS expression was performed as follows. Approximately 10–15 μl extracts from sepal, petal, anther and carpel, and 80–100 μl extracts from root, stem and leaf, were added separately to prewarmed Eppendorf tubes containing 1 ml of assay buffer (extraction buffer containing 1 mM 4-methyl umbelliferyl glucuronide) and incubated at 37° C. A time course was produced by removing 300 μl aliquots and adding them to 2.7ml stop buffer (0.2M $Na_2CO_3$). The incubation was carried out at 37° C. for zero, 30 min. and 60 min. for roots, stems and leaves; zero, 15 min. and 30 min. for sepals, petals, anthers and carpels.

The fluorometer was calibrated by reading a series of concentrations of 4-methyl umbelliferone (from 1 to 100 μM) under different filter and magnification conditions, with excitation at 254–650 nm, emission at 225–650 nm on a Tuner Fluorimeter (Model 112). The rate of increase in fluorescence of samples was measured under the same conditions. A standard of $10^4$ mM 4-MU was used for comparison with each sample reading and stop buffer was used to adjust the fluorometer after each sample measurement.

The specific activity of the GUS enzyme in the extracts was calculated as pmol 4-MU formed per min. per mg total protein added. GUS activity was estimated from the average of the two individual samples and each sample with two repeats. The standard deviation was calculated based on these four repeats.

The quantitative assay of GUS expression in transgenic plants containing the pollen Sta 41promoter/GUS fusion is shown in FIG. 3 (3A, 3B, 3C and 3D). High levels of GUS activity were detected only in extracts from anthers of all these plants. There was no activity in sepals, petals and pistils. In comparison to untransformed Westar, roots and stems showed GUS activity levels 1-2.6-fold and 3.2-11-fold above background levels respectively. Although GUS activity in leaves could be as high as 21-fold above background, the expression in anthers was approximately 99 to 409-fold higher than in leaves where the activity was not observed in the histochemical GUS activity mentioned earlier. The temporal regulation study of the Sta 41 promoter showed that the GUS activity was 2-6-fold higher in 4 mm bud than in 6 mm bud.

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

---

The embodiments of the invention in which an exclusive property or privilege is claimed are defined as follows:

1. An isolated and purified Brassica sp. promoter, which directs expression in the tapetum, wherein said promoter has a nucleotide sequence which has at least 80% homology to SEQ ID NO:1.

2. The promoter according to claim 1, wherein the Brassica sp. is *Brassica napus*.

3. The promoter according to claim 2, wherein said promoter has a nucleotide sequence of SEQ ID NO: 1.

4. A chimeric gene construct comprising a Brassica sp. promoter and the coding sequence of a gene, wherein said promoter directs transcription of the gene in the tapetum, and wherein said promoter has a nucleotide sequence which has least 80% homology to SEQ ID NO: 1.

5. The gene construct according to claim 4, wherein the Brassica sp. is *Brassica napus*.

6. The gene construct according to claim 5, wherein said promoter has a nucleotide sequence of SEQ ID NO: 1.

7. A vector comprising the chimeric gene construct of claim 4.

8. The vector according to claim 7, wherein the Brassica sp. is *Brassica napus*.

9. The vector according to claim 8, wherein said promoter has a nucleotide sequence of SEQ ID NO: 1.

10. A method of conferring tapetum-directed expression on a gene in a plant, comprising:

operatively linking a gene, for which tapetum-directed expression is desired, with a Brassica sp. gene promoter, which directs expression in the tapetum, to produce a chimeric gene, wherein said promoter has a nucleotide sequence which has least 80% homology to SEQ ID NO: 1;

introducing the chimeric gene into an appropriate vector; and introducing the vector into a plant capable of expressing the chimeric gene.

11. The method according to claim 10, wherein the Brassica sp. is *Brassica napus*.

12. The method according to claim 11, wherein said promoter has a nucleotide sequence of SEQ ID NO: 1.

13. A transgenic plant containing the chimeric gene construct of claim 4.

14. The transgenic plant according to claim 13, wherein the Brassica sp. is *Brassica napus*.

15. The transgenic plant according to claim 14, wherein said promoter has a nucleotide sequence of SEQ ID NO: 1.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1960 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO: 1:

```
GAGCTCCACC CACAGAAGCA GATAAACCAG CTGAAGGAAC AACAGAAAAA CCAAAAGATA      60

ATTCGACTGG AGGAGCAGCC GATAAACCAG AAGATAAACC AGTTGGAGGA GCAGCCGATA     120

AACCAGAAGG TAAACCGGAT GGAGGAGCAA CAAATAAGCC AGAAAGTAAA CCAGCTGGAG     180

GACCATCAAA TAAACCAAAA GATAAACCCG CTGGAGGACC AACGGATAAA CCAGAAAGTA     240

AGCCAGCAGA TAAACCCGCT GGAGGACCAA CAGATAAGCC AGGAAGTAAA CCGGTTGATA     300

AACCCGCTGG AGGACCAACA GATAAGACAG AAAGTAAACT GGTTGGAGAG GCATCAAATA     360

AACCAAAAGA TAAACCCGCT GGTGGATCAA CAGATATGCC AGAAGCTGGA GAGACATCAA     420

ATAAACCAAA AGATAAATCC GTTGGAGGAC CAACAAATAA GCCAGAAAGT AAACCAGCTG     480

GAGAAACATC ACATAAACCA AAAGATAAAC CCGCTGGTGG ACCAACAGAT AAGCCAGAAA     540

GTAAACCGGC TGGAGAAACA TCACATAAAC CAAAAGATAA ACTCGCTGGT GGACCAACAG     600

ATAAGCCAGA AAGTAAACCA GCTGGAGAGG CATCAAATAA ACCAAAAGAT AAACCCGCTG     660

GTGGACCAAC AGATAAACCA GCTGGAGGAT CAGTAGATAA ACCAAAAGAT AAACCTGCCG     720
```

```
GAGGACCAAC AGATAAACCA ACAAATAAAC CGACTGGAGG GGCTGCAAAT AAACCGGCTG      780

GAGAGGCAGC AAACAAACCG ACTGGAAAAC CGAAAAATAA ACCGGCTGGA GAGAATAAAC      840

CACCGGGATG GTATAGGTGA ATGGAGTAGT ATGAAATTAA AGTATTGGGT TCCACAAATT      900

ATTCCTAATT TATCCTACAC TACATGTTTC ATAATCATTT CTATAAATGT ACGACTTGTT      960

ACAAAGAAAT GATAAACAGT GTACAGAATT TTCTTTGTAA ATTTATTAAA TTGATGTGGA     1020

TATCATTATA ACTGACGTTA GCGTATATCG ACCAATGCGA TAACCAAATC ATCGGTATAT     1080

ACCTAAGACT TCCTTTTTAA AAATGAATCT GATACTAATT TAATGTACGA CTTCCAATAA     1140

CCAATCTTCT TGCATTTTTC ATTGCCATTT ACCTTGAACG CCTCTCTTTC TAGTATGAGA     1200

CATTAACATT GCGCTCTTGT CACAATGAAG CCATGGAAAA CTTCGGCTCT TTAATCACAC     1260

ATGTGACAAT CCAGTTGGTT TAAGGGAAAG TATTTTATAT TTTATATAGC TCGTTCTCAG     1320

AACAAAAAAA CCAAATTCTT TAGCAAAAAT GGTCCTTAAG GCCCATTCCG TTTCTTCTTA     1380

TAATGTTCTG GGCTAGCCCA TTTGAATTTA AACCTTTCCT TTCAATTTCT GCATTAATAT     1440

AATTCAGTTG TTCAAAAAAA AAATAGCGCT TATTGAAATA ATAGAGAGAA AGATAATGAG     1500

AAGGGAGAAA ATGAAAAGCG TATTTCATAT GAGAGATTGT CAACAAAAAT TGAGTGACTT     1560

TTATGATATT TGTTCAAAGA ATAGTCTAAT AACCTTTCTT ATTTAAATTT TAATTATGTT     1620

ATATATCAAT AATACTAAAA TAATTAGTTA CTCACAGTTC GTGACAAAAA AAAAAGCAAA     1680

TAGATGAAAT GAAATGAAAG AAAGATCTTT CTTCACGCGT TGATATTCAT AAAACAATGG     1740

AATGAAAGAA AACAGTTAAG ATTCTACAAG AAAGAAAAGA AAGTCCCAAA AACATGACAA     1800

ATAGATGAAG AAGCAAATGT GACTTGACGT AACGTAGAAC TCCATATATA CTCCCATCGT     1860

TTTGCATGGA GCATGCATGT GTACCGTGCA CGTCGTAGAC CACACAACTC CTTCATAAAA     1920

AGCCCTCTCT CTTCCCATCA CCAAACCATC AGAAAATATG                           1960

(2) INFORMATION FOR SEQ ID NO: 2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

ATAGGATCCT GATGGTTTGG TGATGGG                                          27
```